United States Patent

Lesho et al.

[11] Patent Number: 5,842,977
[45] Date of Patent: Dec. 1, 1998

[54] MULTI-CHANNEL PILL WITH INTEGRATED OPTICAL INTERFACE

[75] Inventors: Jeffery C. Lesho, Brookeville; Harry A. C. Eaton, Columbia, both of Md.

[73] Assignee: The Johns Hopkins University, Baltimore, Md.

[21] Appl. No.: 685,375

[22] Filed: Jul. 23, 1996

Related U.S. Application Data

[60] Provisional application No. 60/001,378 Jul. 24, 1995.
[51] Int. Cl.$^6$ ........................................................ A61B 5/00
[52] U.S. Cl. ........................... 600/300; 128/903; 250/551; 340/870.17
[58] Field of Search .................................. 128/903, 630, 128/736, 631; 607/60, 30, 31, 32; 250/551; 600/300, 301, 549; 340/870.17

[56] References Cited

U.S. PATENT DOCUMENTS 5,481,262  1/1996  Urbas et al. ............................ 128/903
5,538,007  7/1996  Gorman ................................... 128/903
5,620,473  4/1997  Poore ........................................ 607/31

*Primary Examiner*—Jennifer Bahr
*Assistant Examiner*—Eric F. Winakur
*Attorney, Agent, or Firm*—Eugene J. Pawlikowski; Carla Magda Krivak

[57] ABSTRACT

An optical interface incorporated into a multi-channel telemetry device used principally to provide data representing physiological conditions in a human subject. Information is transmitted without the need of a bio-compatible electrical connection via an optical link which conveys calibration parameters and commands to control the operation of the telemeter. The optical link is configured to reside completely on an integrated circuit chip. Of the three channels designed into the chip by means of appropriate electronic circuitry, one of the channels measures temperature and the other two channels are dedicated to develop generic information selectively derived from other physiological conditions. Calibration information that is programmed into the telemeter by means of the optical interface is retrieved by time division multiplexing with one of the generic channels.

30 Claims, 3 Drawing Sheets

MULTI-CHANNEL PILL WITH INTEGRATED OPTICAL INTERFACE

STATEMENT OF GOVERNMENTAL INTEREST

The Government has rights in this invention pursuant to Contract No. N00039-94-C-0001 awarded by the Department of the Navy.

This application claims the benefit of U.S. Provisional application No. 60/001,378, filed on Jul. 24, 1995.

BACKGROUND OF THE INVENTION

1. Field of the Invention

The invention relates generally to biomedical devices, and particularly to devices of the kind in which medical information is obtained from a human being by measuring certain physiological values without the need for direct contact between the physician and the patient. Implantable/ingestible capsules for generating signals which represent stimuli such as temperature are one example known in the prior art for accomplishing this purpose.

2. Description of the Art

The importance of the invention to biomedical and industrial fields will best be appreciated by reference to and an understanding of several background references relative to temperature measurement.

U.S. Pat. No. 4,844,076 discloses a miniature temperature responsive transmitter that is capable of being encapsulated within a capsule of ingestible size. The circuit design uses a one transistor inverting amplifier with a tank circuit forming the link between the transistor's collector and the battery. The tank circuit is tuned to provide a lagging capacitive load which causes the inverting amplifier to oscillate. The tank circuit contains a coil inductor that emits a near field magnetic communications field containing temperature information. In the patented embodiment the pill uses the inductive coil in the tank circuit as the magnetic pickup to charge a rechargeable nickel cadmium battery.

U.S. Pat. No. 5,415,181 discloses a multi-channel circuit for telemetering signals representing physiological values from a point in a human body to a receiver outside of the body. Two signals $S_1$ & $S_2$ other than a temperature signal are used to provide two frequency modulated signals summed by an amplifier with the summed FM signal then being applied to amplitude modulate a carrier whose frequency varies as a function of temperature. The resulting FM/AM signal is telemetered inductively outside of the body to an external receiver. Appropriate demodulation, filter, and shaping circuits within the external circuit detect the FM signals and thus produce three independent frequencies two of which are related to the original physiological variables and the third being a function of local temperature. Real time plot of the two physiological variables can be obtained using FM discriminators while the temperature dependent frequency is monitored by a counter.

Canadian Patent Application Ser. No. 2,045,507-1 discloses an inductive coupled high temperature monitor that is capable of operating in or nearby conductive objects that produce unwanted reflective impedance. The temperature monitor can be used to telemeter temperature information from a closed soup can or other container, such as during an industrial cooking or heating process.

While these related systems have been found to perform in a satisfactory manner, a specific shortcoming of their design is that they do not take into account the need for automatically telemetering to the external receiver calibration data peculiar to each temperature monitor. In the field of remote monitoring of temperature within an enclosure which has no connecting wires, calibration data for each temperature monitor is generally established in advance of use by manufacturing and testing specifications. The calibration data, once known, is put to use after each temperature readout in order to provide a conversion to true temperature by the external receiver. Current practice in the biomedical field at least is to require the attending medical staff to record beforehand the serial number of the temperature monitor and then adjust the setting of the receiver calibration for the temperature of each patient. A system which does not use a calibration identification signal on the carrier transmitted to the receiver results in unnecessary consumption of time, inefficiency in the use of support staff, and relative insecurity in establishing a bona fide match between a lookup table and an accurate setting at the receiver end.

SUMMARY OF THE INVENTION

Accordingly, one object of the invention is a temperature monitor with a calibration signature imposed on the signal telemetered from the environment in which the monitor is enclosed.

Another object is to relieve members of attending support personnel from recording the serial number of a temperature monitor and then setting manually the receiver calibration for each transducer as the temperature is recorded.

A further object of the invention is to equate a serial number of a temperature monitor to the temperature calibration for that unit.

Yet another object is to obviate calibration lookup when examining telemetered results of temperature taken from the interior of an enclosure under observation.

Still a further object is to reduce error in miniature precision temperature monitors and minimize bookkeeping requirements in biomedical and other applications.

In the present invention, as it relates to a multi-channel system designed to fulfill a need in diagnostic procedures, an optical interface is incorporated into a multi-channel telemetry device to allow for communication to a packaged telemeter. Information transmitted on the optical link includes calibration parameters and commands to control the operation of the telemeter. One of three channels of a telemeter is dedicated to temperature measurement, while the other two channels are assigned to making generic measurements. The generic channels carry information from transducers that are interfaced to the system through on-chip general purpose operational amplifiers. The calibration information for each transducer is optically communicated and stored electronically at the time of dispersal and is retrieved by time division multiplexing it with one of the generic channels.

Other objects will become apparent from the following detailed description of the embodiment of the invention when taken in conjunction with the accompanying drawings.

DETAILED DESCRIPTION OF THE PREFERRED EMBODIMENTS

The following U.S. patents, assigned to the same assignee as the present application, are related to the present invention, and the teachings of the patents are hereby incorporated by reference:

U.S. Pat. No. 4,844,076, for Ingestible Size Continuously Transmitting Temperature Monitoring Pill.

U.S. Pat. No. 5,415,181, for AM/FM Multi-Channel Implantable/Ingestible Biomedical Monitoring Telemetry System.

Figure 1:
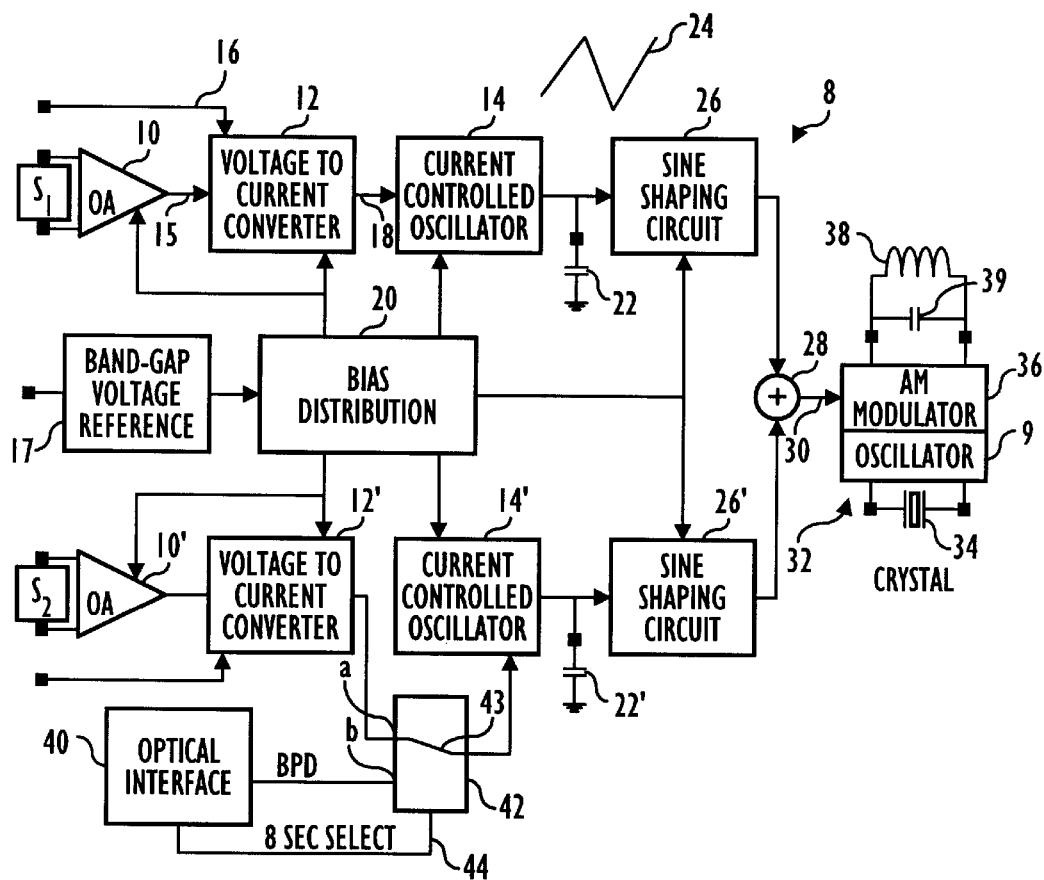
FIG. 1 is a schematic drawing of a multi-channel telemeter having an optical interface embodying the invention.

Referring to FIG. 1, the multi-channel telemetry system with optical interface of the present invention, generally designated as the telemeter 8, is adapted to transmit electrical signals which correspond to physiological or physical measurements made in an enclosure, such as a cavity of the human body. Such signals are telemetered from one point to a second remote point and comprise at least two signals which represent a variable measured in conjunction with a simultaneously developed temperature signal. To illustrate the invention in its simplest form, it will be assumed that the telemetering is intended to transmit three signals two of which are derived from sensors $S_1$ and $S_2$ and the third being generated by an oscillator 9 whose output signal concerns temperature within an enclosure. The sensors $S_1$ and $S_2$ may be of any known form for biological or non-biological purposes.

Turning now to the three-channel telemetry system of the invention as embodied in FIG. 1, the system is arranged to transmit signals over three channels. As shown in FIG. 1, a low frequency channel is characterized as having an input signal from $S_1$ which is applied to an op-amp 10 band limited, for example, from 0 to 250 Hz. A high frequency channel supplied with an input from signal $S_2$ is characterized by an op-amp 10' band limited from 0 to 1300 Hz. As will be described, the FIG. 1 embodiment employs a combination of frequency modulation and amplitude modulation functions to fulfill a need in diagnostic medicine to measure physiological variables at the point of origin within a human body without prolonged invasive procedures. It will be understood, therefore, that only the operation of the low frequency or upper channel in FIG. 1 will be described for the moment as the two channels downstream of the op-amps 10 and 10' operate identically and differ from each other only in the center frequency of their respective current controlled oscillators and the optical interface of the invention.

The sensor input $S_1$ to the low frequency or upper channel is amplified and conditioned by op-amp 10. The input transistor in the op-amp is a MOSFET and so it has inherently high input impedance and low bias current. The amplified sensor signal from op-amp 10 is converted to a current by means of a voltage to current converter 12 to drive a current controlled oscillator 14. The voltage to current converter 12 has a differential input between terminals 15 and 16 thereof whose form depends upon the interface between the op-amp 10 and the physiological junction under observation. In a typical case, and as shown herein, the voltage to current converter 14 is provided with a positive lead 15 internally connected to the op-amp output and a negative lead 16 available for user connection to a reference point.

The input stage to the voltage to current converter 12 is also a high impedance MOSFET input. The differential input voltage into converter 12 is driven across an on-chip 100 KΩ resistor (not shown) to produce an output current fed to the current controlled oscillator 14. A fixed offset current (normally 10 μA) derived from a band-gap voltage reference 17 is added to line 18 from a bias distribution 20. The offset current, when combined with the differential input to voltage to current converter 12 between terminals 15 and 16, sets the center frequency of the current controlled oscillator 14 thus allowing both positive and negative deviations of the differential voltage input.

The current into the current controlled oscillator 14 programs the magnitude of the current through an external capacitor 22. The capacitor 22 is thus charged and discharged between two fixed voltages. When the voltage on capacitor 22 reaches one of the voltage trip points, the direction of the capacitor current is reversed as shown by the waveform 24. The resulting output of the current controlled oscillator 14 is a triangular wave which varies between two voltages (nominally 400 mV and 800 mV) as established by the bandgap voltage reference 17. It has been found that using voltages from the bias distribution 20 and referencing them to the band-gap voltage reference 17 advantageously reduces sensitivity to both supply voltage and temperature variations.

The instantaneous frequency of the current controlled oscillator 14 may be described by equation 1:

$$f=(1.0+Vd)(0.8\ RC) \tag{1}$$

where Vd is the differential voltage between terminals 15 and 16 at the input of voltage to current converter 12, R is 100 kΩ and C is the value of the external capacitor 22. Equation 1 shows that the signal of interest frequency modulates the waveform of the current controlled oscillator 14. The frequency modulation of the sensor input at op-amp 10 allows constant voltages to be measured. In addition, the current controlled oscillators are designed for wide-band fm modulation in order to maintain dc accuracy. Constant voltages or currents may be produced by a variety of sensors including strain gauges, chemical sensors and others.

The triangular wave 24 from the current controlled oscillator 14 contains odd harmonics of the fundamental frequency of oscillator 14. It is recognized that the harmonics from the low frequency or upper channel may fall into the band allocated to the high frequency or lower channel and may cause interference problems. To minimize such interference, the low frequency or upper channel shown in FIG. 1 has the developed signal passing through a sine shaping circuit 26. The sine shaping circuit 26 substantially attenuates the odd harmonics present in the triangular wave 24 and is preferably employed because it uses much less chip area than filter circuits, requires no external parts, reduces the cross-talk between the sub-carriers, and provides maximum flexibility for configuring the sub-carrier channels.

In the summing amplifier 28, the two shaped signals from the low and high frequency channels are summed to produce a combined signal on line 30 that contains all of the desirable information from the two sensor inputs at op-amps 10, 10'. The signals from sine shaping circuits 26 and 26' can conveniently be summed because the center frequencies of the current controlled oscillator and frequency deviations are chosen to limit the amount of cross talk between the low and high frequency channels.

As further shown in FIG. 1, a third channel generally designated 32 is dedicated to measurement of the physiological temperature of importance during an examination or experiment involving a subject, whether human, animal, or physical. The transducer in the channel 32 is a temperature sensitive crystal 34 which swings the frequency of oscillator 9 about a base frequency of approximately 262 Khz. The output of oscillator 9 is amplitude modulated in AM modulator 36 by the output of summing amplifier 28. The final signal, which contains two FM signals amplitude modulated onto the temperature signal, drives a small coil 38 that transmits the signal. The coil 38 generates a magnetic field that is inductively coupled to an external receiver not shown in FIG. 1, but understood to be similar in form and function to the external receiver described in connection with the embodiment shown in FIG. 1 of U.S. Pat. No. 5,415,181. In practice, the temperature sensing crystal 34 used to generate the AM carrier resonates at approximately 262 Khz at 25° C. and nominally varies 9 Hz/°C. In practice, the temperature measurement can be calibrated to better than 0.1° C.

Accordingly, although not shown in the FIG. 1 embodiment, it will be understood that the signal transmitted by coil 38 is picked up by an external receiver coil, amplified appropriately, and directed over three separate paths, one for the temperature signal, and one each for the biological inputs sensed at the op-amps 10 and 10'. As further will be understood from the description of FIG. 1 and the previously referred to U.S. Pat. No. 5,415,181, the signals produced by the low and high frequency channels are generated by demodulating the signals produced by the current controlled oscillators 14 and 14'. Band pass filters are used to extract the individual FM channel signals. The separated signals are then individually FM demodulated by phase lock loop circuits. A final filter to remove the FM carrier frequencies provides the two measured physiological variables. Appropriate demodulation occurs simultaneously to produce a signal proportional to the temperature affecting the crystal 34. It will thus be understood that the demodulation products of the receiver actively associated with the invention embodiment shown in FIG. 1 are faithful replicas of the input signals $S_1$ and $S_2$ and the output of oscillator 9.

As was discussed hereinabove, one problem with the use of a monitor of the type embodying the present invention in a clinical setting is the need to keep track of the calibration for each sensor while transferring a single receiver in the clinic from patient to patient. Currently, the calibration information must be manually entered into the receiver each time a new patient undergoes examination. Ideally, and as conceived by the present invention, the calibration figures for each transducer should reside in the telemeter circuit and be transmitted along with the data signals. The receiver can then read the data signals and automatically apply the calibration adjustment, if any, and then display the physiological information in clinical units.

Referring again to FIG. 1, in accordance with the present invention, an optical interface 40 is arranged for optical coupling to current controlled oscillator 14' by means of a multiplexer shown herein for simplicity, as having an arm 43 moveable between high and low contacts a and b, respectively, under the control of an intermittent signal on line 44 in a manner to be described. The optical link, when established between interface 40 and an external light programmer 45 (FIG. 2) eliminates the need for connections through seals and the like when programming an implantable or ingested device.

Figure 2:
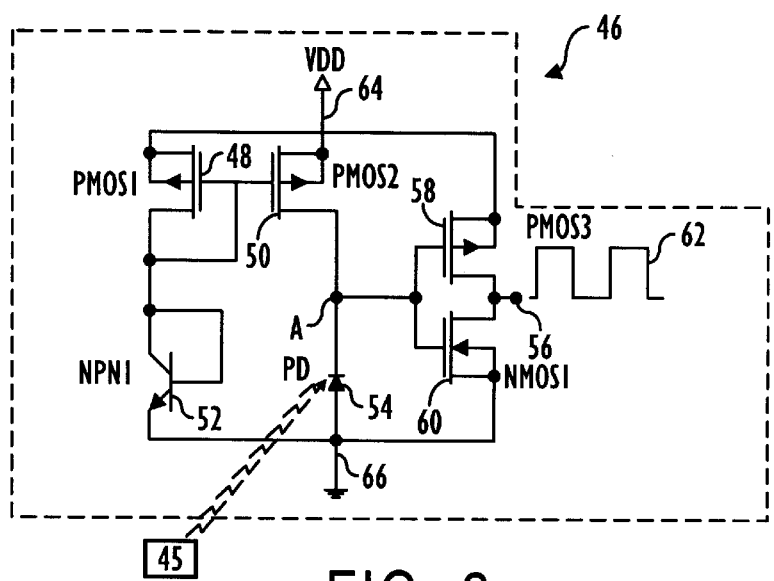
FIG. 2 shows the photodiode amplifier used in connection with the telemeter shown in FIG. 1.

Reference is now made to FIG. 2 which shows a one-bit analog to digital converter and photodiode amplifier generally designated 46. Metal oxide semiconductor transistors 48 and 50 and bipolar junction transistor 52 together with photodiode 54 form a light sensitive circuit that produces a digital signal at output terminal 56 of an inverter formed by metal oxide semiconductor transistors 58 and 60. When light from programmer 45 strikes the photodiode 54, the digitized signal 62 shown at terminal 56 mimics the light impulses activating photodiode 54 by swinging between the limits of VDD on line 64 and ground at line 66. In principle, the optical communication could be conducted through the skin for an implanted device provided that the external source of light is bright enough. In actual practice, the circuit shown in FIG. 2 is contained in optical interface 40 which is fabricated on a chip represented by and containing all of the elements shown in FIG. 1 except for the capacitors 22, 22", the crystal 34, coil 38, capacitor 39, and sensors S1 and S2. One optimum design of photodiode 54 has a dimension of 240 μm by 240 μm and includes a series of four concentric N+, 10 μm wide rings which act as charge capturing rings to pick up the photo-currents. The anode of photodiode 54 is connected to ground 66 through the P substrate of the wafer and its cathode is connected in common with transistors 50, 58 and 60. Photons create electron-hole pairs in the lattice that are separated by the electric field and are attracted to the cathode and the holes are picked up by the anode. This creates a current in the direction from the cathode to the anode, thus discharging the anode. The perimeter of photodiode 54 is a grounded charge sink that protects the surrounding circuitry from any photo-currents. The entire chip, except for the photodiode, is covered with a top layer of metal during the integrated circuit (IC) fabrication process. This provides a measure of masking for the digital portions of the chip that must function during the light exposure as calibration and control data are being introduced to the chip at the time it is manufactured.

When photodiode 54 is activated by an external light source (not shown) the output at terminal 56 is high. In the absence of an activating beam of light, the output at terminal 56 is low. Transistors 48 and 52 form the programming side of a current mirror. The current is determined by the length to width ratio of transistors 48 and 50. A fixed current is programmed to supply photodiode 54 and charge Node A. When photodiode 54 is activated, Node A becomes discharged and the voltage pulse is inverted to form a high output at terminal 56. When the photodiode is off, no current flows through the reverse biased photodiode thereby charging Node A to VDD and thus producing a low output from the inverter transistors 58 and 60. The principal function therefore of the inversion is to condition the digitized waveform on terminal 56 and make it compatible with the digital logic of the downstream circuit it drives.

Once the digitized waveform is produced at terminal 56, it is compatible with all of the other digital circuitry contained on the chip. The first digital light pulse powers up decoding and oscillator circuits. The falling edge of the first digital pulse determines the timing of all subsequent bits. The shift registers are programmed to operate for a predetermined period of time (preferably in seconds) or else the decoding circuitry shuts down. The telemeter is commanded to turn off after a period of operation by transmitting a command that changes the proper bit in the controlling register. That portion of optical interface 40 which contains the digital decoding and register elements responsive to the output of the circuit shown in FIG. 2 is shown in FIG. 3.

Figure 3:
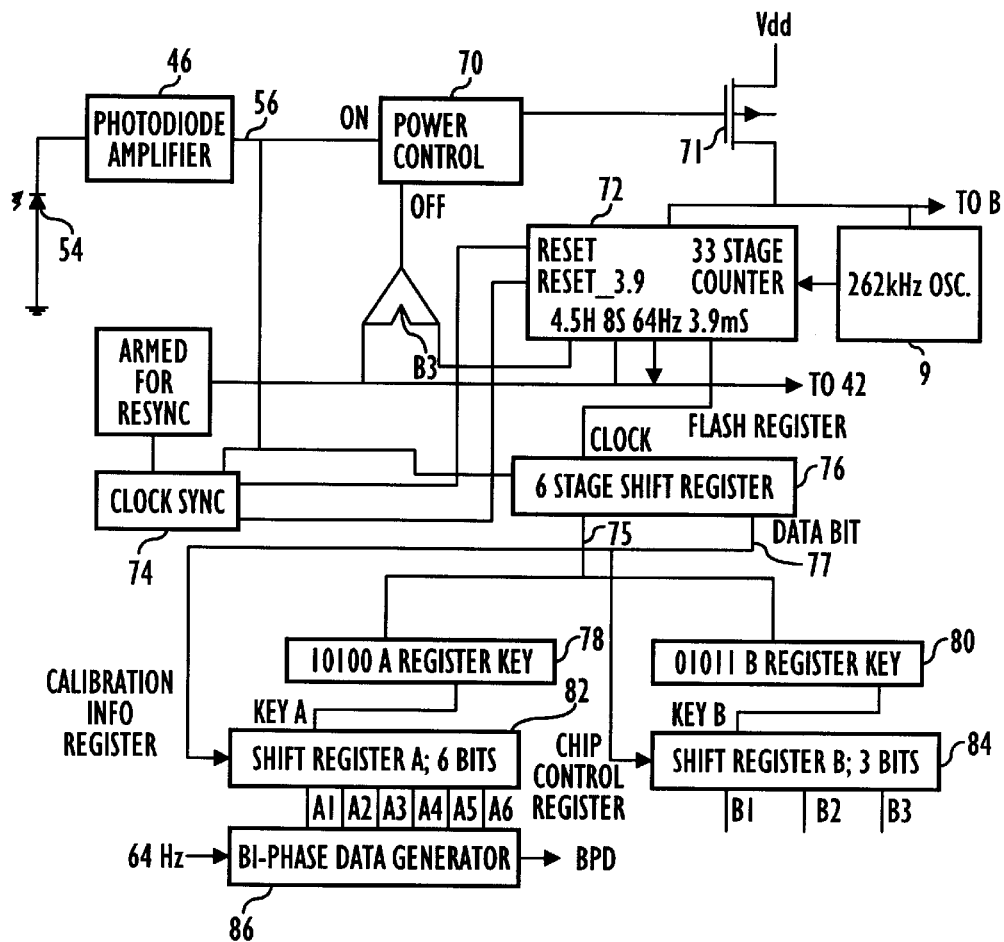
FIG. 3 shows the digital decoding and register system used in connection with the optical interface shown in FIG. 1.

As indicated in FIG. 3, the rising edge of the digitized signal at terminal 56 sets a power control 70 whose activation of PMOS transistor 71 results in power being applied to 33 stage counter 72, oscillator 9 and telemeter 8. Clock sync 74 and six stage shift register 76 also are connected to be responsive to the signal on terminal 56. The falling edge of the first digitized pulse resets counter 72 and all timing is determined from the falling edge of the pulse. The bit length is 3.9 mS. That is, the first bit is clocked 1 Bit time from the falling edge and every 3.9 mS after that. All bits are determined by the state of the digitized signal when a bit is clocked.

Shift register 76 has two output lines the first of which 75 is connected to A and B register keys 78 and 80, respectively, and the second of which 77 is connected to A and B shift registers 82 and 84, respectively. The registers 82 and 84 are programmed by flashing one data bit over line 77 followed by a specific pattern of five bits on line 75. Therefore, for completely programming a register, six times the number of bits in the register must be flashed. Registers 82 and 84, moreover, are filled in a first in first out fashion. A register 82 is 6 bits long and B register 84 is 3 bits long. The lengths specified for registers 82 and 84 are completely arbitrary and depend primarily on the chip area available and the application need. Register A 82 is programmed by flashing a data bit then the digital sequence 10100. Register B 84 is programmed by flashing a data bit followed by the digital complement sequence 01011. The sequences were chosen because they cannot be duplicated for either type of data bit, that is, as the bits cycle through the keys 78 and 80, a series of bits cannot arbitrarily program a register. Once the register key 78 recognizes the command pattern 10100 at shift register 76 it keys shift register 82 to load a single data bit from shift register 76. As will be apparent from FIG. 4, additional sequences are used to program the balance of bits to be stored in the A and B registers. The bi-phase generator 86 uses the data stored in register 82 to generate a bi-phasic signal. The output of generator 86 thus represents the calibration information programmed through multiplexer 42 into the lower channel during the 8-second multiplexing interval.

It will thus be understood that the calibration information produced by optical interface 40 is delivered in eight second bursts in the lower of the two telemeter channels as pictured in FIG. 1. The calibration data is transmitted in bi-phase form thus causing the carrier of oscillator 9 to jump between two fixed frequencies. Table 1 shows the patterns needed to program data in the registers 82 and 84.

TABLE 1

| Bits input left to right | REGISTER A | REGISTER B |
|---|---|---|
| DATA 0 | 010100 = a | 001011 = b |
| DATA 1 | 110100 = A | 101011 = B |

As shown in Table 1, the patterns to program data in a register are entered left to right with the data bit first. These patterns are grouped together to form chains that are used to place a specific value in a register. For example, to put the number 13 in the digital expression 10101 into the A register 82 the group AaAaAa is flashed. To program the Bit B3 to a 1, in order to control the length of the telemeter operation, three bits must be sent to register 84 . The group Bbb would load register 84 [B1B2B3]=[001].

Figure 4:
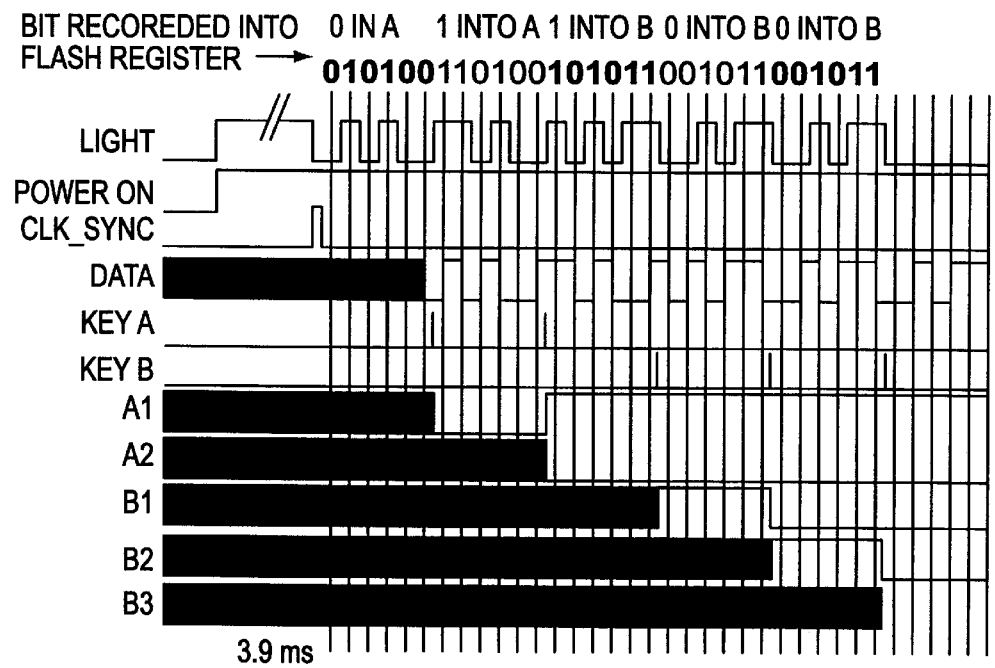
FIG. 4 shows the timing for programming data into the A and B shift registers shown in FIG. 3.

A more favorable understanding of the timing for programming data into both registers 82 and 84 may be had by reference being made to FIG. 4.

Figure 5:
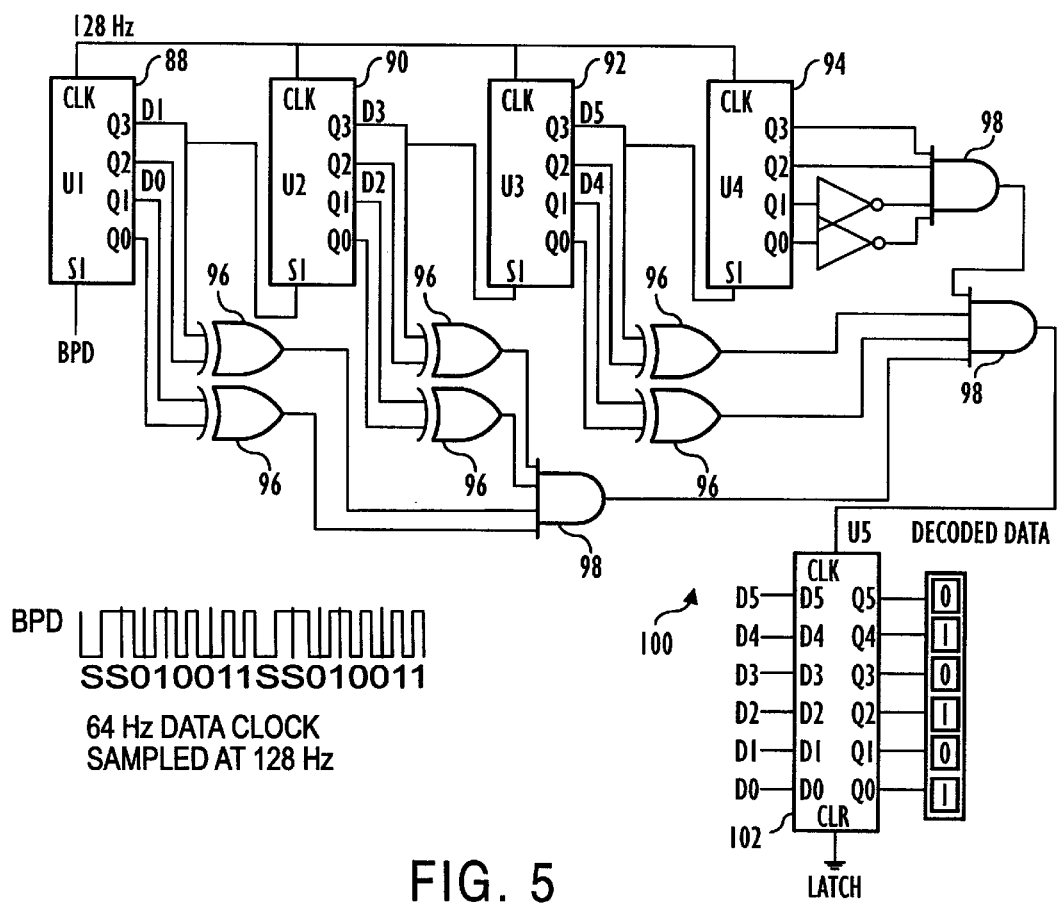
FIG. 5 shows one exemplary circuit in the external receiver to decode the calibration signature imposed on the data transmitted from the telemeter shown in FIG. 1.

Having described the manner in which the calibration information for the sensors $S_1$, and $S_2$ and the crystal 34 are programmed into the signal transmitted by the telemeter 8, one form of the external receiver and data signature decoder for acquiring the digital calibration signal will now be described with reference being made to FIG. 5. As shown in FIG. 5, the output bi-phase data from the external demodulator is applied to a 16-bit shift register 100 comprised by four 4-bit registers 88, 90, 92 and 94 appropriately arranged in a manner well known in the art with OR gates 96 and AND gates 98. The output of the 16-bit register feeds into a latch 102 the output of which is used to latch the decoded calibration signature presented, by way of example, as digital number 13. As indicated in FIG. 5, the bi-phase data is sampled at twice the bit rate (128 Hz), thereby producing samples of each phase of each bit. The synchronization levels are also sampled twice. In the 16-bit register each set of adjacent bits is XOR'd. The XOR produces a 1 when either a bi-phase 1 or 0 is in that set of two bits. Only when a valid chain of bits is sensed is the latch clocked. The second phase of each bit is latched as this is the phase that represents the bit. Because the data is transmitted in bi-phasic form, with a synchronization signal and repetitive data, the system can synchronize after two cycles of data.

Thus, there has been provided, in accordance with the present invention, a very small telemetry system in which temperature is one variable that is always measured. The temperature transducer is a crystal designed to have a large linear frequency versus temperature characteristic. Because this transducer is required to generate the AM carrier for the two generic channels, temperature is always available from the system. As one example of the method of calibrating a temperature transducer, if a 32-bin grid is drawn with 25° C. frequency offset on the top and slope on the side, each temperature sensitive crystal will fall into a bin. When this bin number is programmed into the telemeter as the calibration, the external receiver can look up the calibration from the bin number and immediately apply it to the measured frequency. The same procedure can be applied to the sensors used in the generic channels. More bits will be required to hold all the calibration for temperature and two channels, but this creates no problem as the system is easily expandable.

What is claimed is:

1. A system for improving the correlation between an output of a sensor and calibration data established for that sensors. comprising:

an integrated circuit chip;

a sensor connected to said chip for producing a first signal having a value dependent upon the measurement of a physiological parameter;

a light detector integrated on said chip;

means for producing light pulses for illuminating said light detector to produce a second signal which represents calibration data for said sensor;

memory means for storing information from said second signal;

an external receiver; and means for telemetering said first signal and the calibration data concurrently to said receiver.

2. A system in accordance with claim 1, wherein said sensor is a temperature sensitive crystal.

3. A system in accordance with claim 1, wherein said calibration data transmitted to said receiver is combined with said first signal.

4. A system for improving the correlation between an output of a sensor and calibration data established for that sensor, comprising:

an integrated circuit chip;

a sensor connected to said chip for producing a first signal having a value dependent upon the measurement of a physiological parameter;

a light detector integrated on said chip;

means for producing light pulses for illuminating said light detector to produce a second signal stored in said chip and subsequently read out when said chip is activated, said stored signal representing the calibration data for said sensor;

a current controlled oscillator receiving the calibration data as an input;

a sine shaping circuit receiving an output from said oscillator for substantially attenuating any odd harmonics present in an output from said oscillator and producing an output signal;

means for amplitude modulating said first signal by the output signal from said sine shaping circuit to produce a third signal; and means for telemetering said third signal to an external receiver.

5. A system in accordance with claim 4, wherein said sensor is a temperature sensitive crystal.

6. A system in accordance with claim 4, wherein said calibration data transmitted to said external receiver is combined with said first signal.

7. A system for propagating a signal from a sensor located inside a human body to a point outside the body which requires correlation between an output of the sensor and calibration data established for that sensor, comprising:

an integrated circuit chip;

a sensor connected to said chip for producing a first signal having a value dependent upon the measurement of a physiological parameter detected within a human body;

a light detector integrated on said chip;

means for producing light pulses for illuminating said light detector to produce a second signal which represents the calibration data for said sensor;

memory means for storing information from said second signal; and means for concurrently telemetering said first signal and contents of said memory means to and external receiver.

8. A system in accordance with claim 7, wherein said sensor is a temperature sensitive crystal.

9. A system in accordance with claim 7, wherein said contents of said memory means transmitted to said external receiver is combined with said first signal.

10. A system for propagating a signal from a sensor located inside a human body to a point outside the body which requires correlation between an output of the sensor and calibration figures for that sensor, comprising:

an integrated circuit chip;

a sensor connected to said chip for producing a first signal having a value dependent on the measurement of a physiological parameter detected within a human body;

a light detector integrated on said chip;

means for producing light pulses for illuminating said light detector to produce a second signal stored in a memory on said chip and subsequently read out when said chip is activated, said stored signal representing the calibration data for said sensor;

a current controlled oscillator receiving said calibration data as its input;

a sine shaping circuit receiving an output of said oscillator and substantially attenuating any odd harmonics present in the output of said oscillator;

means for amplitude modulating said first signal by the output signal from said sine shaping circuit to produce a third signal; and means for telemetering said third signal to an external receiver.

11. A system in accordance with claim 10, wherein said sensor is a temperature sensitive crystal.

12. A system in accordance with claim 10, wherein said calibration data transmitted to said external receiver is combined with said first signal.

13. A system in accordance with claims 1, 4, 7, or 10, wherein said sensor is a temperature sensitive crystal which resonates at approximately 262 Khz at 25° C.

14. A system according to claim 13, wherein said system further comprises additional sensors for producing additional signals dependent upon the measurement of additional parameters and said means for telemetering includes means for simultaneously telemetering said additional signals with said first signal and said calibration data using frequency division multiplexing.

15. A system in accordance with claims 1, 4, 7, or 10, wherein said light detector is a photodiode.

16. A system according to claim 15, wherein said system further comprises additional sensors for producing additional signals dependent upon the measurement of additional parameters and said means for telemetering includes means for simultaneously telemetering said additional signals with said first signal and said calibration data using frequency division multiplexing.

17. A system for propagating a signal from a sensor located inside an enclosure to a point outside the enclosure which requires correlation between an output of the sensor and calibration data established for that sensor, comprising:

an integrated circuit chip;

a sensor connected to said chip for producing a first signal having a value dependent upon the measurement of a parameter inside an enclosure;

a light detector integrated on said chip;

means for producing light pulses for illuminating said light detector to produce a second signal which represents the calibration data for said sensor;

memory means for storing information from said second signal;

an external receiver; and means for telemetering said first and second signals concurrently to said receiver.

18. A system in accordance with claim 17, wherein said sensor is a temperature sensitive crystal.

19. A system in accordance with claim 17, wherein said calibration data transmitted to said external receiver is combined with said first signal.

20. A system for improving the correlation between the output of a sensor and the calibration data established for that sensor, comprising:

an integrated circuit chip;

a sensor connected to said chip for producing a first signal having a value dependent upon a physical measurement;

a light detector integrated on said chip;

means for producing light pulses for illuminating said light detector to produce a second signal which represents the calibration data for said sensor;

memory means for storing information from said second signal;

an external receiver;

means for combining said first signal and said stored information producing a third signal; and means for telemetering said third signal to said external receiver.

21. A system in accordance with claim 20, wherein said sensor is a temperature sensitive crystal.

22. A system according to claims 1, 3, 4, 6, 7, 9, 10, 12, 17, 19 or 20, further comprising identification data included in said calibration data.

23. A system according to claim 22, wherein said system further comprises additional sensors for producing additional signals dependent upon the measurement of additional parameters and said means for telemetering includes means for simultaneously telemetering said additional signals with said first signal and said calibration data using frequency division multiplexing.

24. A system according to claims 1, 3, 4, 6, 7, 9, 10, 12, 17, 19 or 20, further comprising identification data time multiplexed into said first signal.

25. A system according to claim 24, wherein said system further comprises additional sensors for producing additional signals dependent upon the measurement of additional parameters and said means for telemetering includes means for simultaneously telemetering said additional signals with said first signal and said calibration data using frequency division multiplexing.

26. A system according to claim 1, 3, 4, 6, 7, 9, 10, 12, 17, 19, or 20, wherein said system further comprises additional sensors for producing additional signals dependent upon the measurement of additional parameters and said means for telemetering includes means for simultaneously telemetering said additional signals with said first signal and said calibration data using frequency division multiplexing.

27. A method for improving the correlation between an output of a sensor and calibration data established for that sensor comprising the steps of:

(a) providing an integrated circuit chip connected to said sensor;

(b) integrating a light detector on said chip;

(c) producing light pulses for illuminating said light detector at the time of manufacture of said chip to produce a signal which represents the calibration data for said sensor stored in a memory on said chip; and (d) activating said sensor at the time of installation to read out said stored signal.

28. A method in accordance with claim 27, wherein said light detector comprises a photodiode.

29. A method according to claim 27, wherein said calibration data according to step (c) includes identification data.

30. A method according to claim 27, further comprising the steps of:

(e) producing additional signals dependent upon the measurement of additional parameters; and, (f) simultaneously telemetering the additional signals with the first signal and the calibration data by frequency division multiplexing.

* * * * *